US012611475B2

(12) United States Patent　(10) Patent No.:　US 12,611,475 B2
Garcia Gonzalez et al.　(45) Date of Patent:　Apr. 28, 2026

(54) SYSTEM FOR IMPLANTATION BY STERILISATION TECHNIQUES

(71) Applicant: Universidade de Santiago de Compostela, Santiago de Compostela (ES)

(72) Inventors: Carlos Alberto Garcia Gonzalez, Santiago de Compostela (ES); Victor Santos Rosales, Santiago de Compostela (ES); Maria Beatriz Magariños Ferro, Santiago de Compostela (ES); Carmen Alvarez Lorenzo, Santiago de Compostela (ES)

(73) Assignee: Universidade de Santiago de Compostela, Santiago de Compostela (ES)

( * ) Notice: Subject to any disclaimer, the term of this patent is extended or adjusted under 35 U.S.C. 154(b) by 438 days.

(21) Appl. No.: 18/033,228

(22) PCT Filed: Oct. 22, 2021

(86) PCT No.: PCT/ES2021/070768
§ 371 (c)(1),
(2) Date: Apr. 21, 2023

(87) PCT Pub. No.: WO2022/084569
PCT Pub. Date: Apr. 28, 2022

(65) Prior Publication Data
US 2023/0390442 A1　Dec. 7, 2023

(30) Foreign Application Priority Data
Oct. 23, 2020　(ES) ............................... ES202031065

(51) Int. Cl.
| | |
|---|---|
| *A61L 9/00* | (2006.01) |
| *A61K 38/47* | (2006.01) |
| *A61K 39/00* | (2006.01) |
| *A61L 2/00* | (2006.01) |
| *A61L 2/07* | (2006.01) |
| *A61L 2/186* | (2026.01) |
| *B01D 11/02* | (2006.01) |
| *B01J 3/04* | (2006.01) |

(52) U.S. Cl.
CPC ................. *A61L 2/186* (2013.01); *A61L 2/07* (2013.01); *B01J 3/04* (2013.01)

(58) Field of Classification Search
CPC .... A61L 2/00; A61L 2/18; A01N 1/00; A01N 59/04; C07K 14/51
USPC ....... 422/4, 28, 32–33, 292, 295; 424/94.61, 424/184.1
See application file for complete search history.

(56) References Cited

U.S. PATENT DOCUMENTS

| | | | |
|---|---|---|---|
| 6,149,864 | A | 11/2000 | Dillow et al. |
| 7,988,892 | B2 | 8/2011 | Eisenhut et al. |
| 2004/0120852 | A1 | 6/2004 | Kanno |
| 2007/0003432 | A1 | 1/2007 | Christensen et al. |
| 2009/0041620 | A1 | 2/2009 | Burns et al. |
| 2009/0134542 | A1* | 5/2009 | Eisenhut ................... A61L 2/18 264/83 |
| 2010/0080790 | A1 | 4/2010 | Matthews et al. |
| 2011/0236256 | A1 | 9/2011 | Matthews et al. |
| 2014/0193552 | A1 | 7/2014 | Burns et al. |

FOREIGN PATENT DOCUMENTS

| | | |
|---|---|---|
| EP | 1782839 A1 | 5/2007 |
| WO | 99/66960 A2 | 12/1999 |
| WO | 2017/161196 A1 | 9/2017 |
| WO | 2019168428 A1 | 9/2019 |

OTHER PUBLICATIONS

Makadia HK, Siegel SJ, Poly-lactic-co-glycolic acid (PLGA) as biodegradable controlled drug delivery carrier. Polym 3, 1377-1397, 2011.

Dash T.K, Konkimalla V.B. Poly(-e-caprolactone) based formulations for drug delivery and tissue engineering: A review. J. Controlled Release, 2012, 158, 15-33.

Abedalwafa M, Wang F, Li C. Biodegradable poly-epsilon-caprolactone (PCL) for tissue engineering applications: A review. Rev. Adv. Mater. Sci, 2013, 34, 123-140.

Rutala W.A, Weber D.J, and the Healthcare Infection Control Practices Advisory Committee. "Guideline for Disinfection and Sterilization in Healthcare Facilities, 2008" Centers for Disease Control and Prevention. 2008.

White A, Burns D, Christensen TW, Effective terminal sterilization using supercritical carbon dioxide. J BiotechnoL 2006, 123 (4), 504-15.

Díaz-Gómez L, Yang F, Jansen J.A, Concheiro A, Alvarez-Lorenzo C, Garcia-González CA. Low viscosity-PLGA scaffolds by compressed CO2 foaming for growth factor delivery. RSC Adv, 2016, 6, 70510-70519.

Ribeiro N, Soares GC, Santos-Rosales V, Concheiro A, Alvarez-Lorenzo C, Garcia-González CA, Oliveira AL, A new era for sterilization based on supercritical CO2 technology, J Biomed Mater Res. 2020, 108(2), 399-428.

Rezvan K, Chen QZ, B laker JJ, Boccaccini AR, Biodegradable and bioactive porous polymer /inorganic composite scaffolds for bone tissue engineering, Biomater. 2006, 27, 3413-3431.

Bernhardt A, Wehrl M, Paul B, Hochmuth T, Schumacher M, et al. Improved Sterilization of Sensitive Biomaterials with Supercritical Carbon Dioxide at Low Temperature. PLOS on. 2015, 10 (6): e0129205.

Lanzalaco S, Campora S, Brucato V, Carfi Pavia F, Di Leonardo ER, Ghersi G, et al. Sterilization of macroscopic poly (-lactic acid) porous scaffolds with dense carbon dioxide: Investigation of the spatial penetration of the treatment and of its effect on the properties of the matrix. J Supercrit Fluids. 2016, 111:83 90.

(Continued)

*Primary Examiner* — Monzer R Chorbaji
(74) *Attorney, Agent, or Firm* — Dykema Gossett PLLC

(57) ABSTRACT
A system for implantation by sterilisation techniques. A sterile implantation system comprising a heat-sensitive polymeric matrix that modifies its structure in the presence of a compressed gas or supercritical fluid to produce a solid or semi-solid with porosity greater than 60%.

19 Claims, 6 Drawing Sheets

(56)         References Cited

OTHER PUBLICATIONS

Scognamiglio F, Blanchy M, Borgogna M, Travan A, Donati I, Bosmans JWAM, et al. Effects of supercritical carbon dioxide sterilization on polysaccharidic membranes for surgical applications. Carbohydr Polym. 2017, 173:482-8.

Ruphuy G, Souto-Lopes M, Paiva D, Costa P, Rodrigues AE, Monteiro FJ, et al. Supercritical CO2 assisted process for the production of high-purity and sterile nano-hydroxyapatite/chitosan hybrid scaffolds. J Biomed Mater Res B Appl Biomater. 2018, 106(3):965-75.

Karageorgiou V, Kaplan D, Porosity of 3D biomaterial scaffolds and osteogenesis, Biomaterials, vol. 26, Issue 27, Sep. 2005, pp. 5474-5491.

Zadpoor AA, Bone tissue regeneration: the role of scaffold geometry, Biomater. Sci., 2015, 3, 231-245.

ISO 14937:2009 Sterilization of health care products—General requirements for characterization of a sterilizing agent and the development, validation, and routine control of a sterilization process for medical devices. International Organization for Standardization, 2009.

Soares GC, Learmonth DA, Vallejo MC, Davila SP, González p. Sousa RA, et al. Supercritical CO2 technology: The next standard sterilization technique? Materials Science and Engineering: C, vol. 99, Jun. 2019, pp. 520-540.

Dai Z, Ronholm J, Tian Y, Sethi B, Cao X. Sterilization techniques for biodegradable scaffolds in tissue engineering applications. J Tissue Eng. 2016, 7, 204173141664881.

International Search Report for related patent application PCT/ES2021/070768, prepared by the Spanish Patent and Trademark Office and issued on Jan. 20, 2022, in Spanish.

Translation into English of the International Search Report for related patent application PCT/ES2021/070768, prepared by the Spanish Patent and Trademark Office and issued on Jan. 20, 2022.

Written Opinion of the International Searchng Authority for related patent application PCT/ES2021/070768, prepared by the Spanish Patent and Trademark Office and issued on Jan. 20, 2022, in Spanish.

Machine translation into English of the Written Opinion of the International Searchng Authority for related patent application PCT/ES2021/070768, prepared by the Spanish Patent and Trademark Office and issued on Jan. 20, 2022.

* cited by examiner

SYSTEM FOR IMPLANTATION BY STERILISATION TECHNIQUES

CROSS-REFERENCE TO RELATED APPLICATION

This application is a national stage filing based upon International application No. PCT/ES2021/070768, filed 22 Oct. 2021, which claims the benefit of priority to Spain application No. P202031065, filed 23 Oct. 2020.

TECHNICAL FIELD

The invention relates to a sterile system for implantation. More specifically, the system comprises a matrix which is thermosensitive, and which modifies its structure in the presence of a compressed gas or a supercritical fluid. The invention also relates to a process for the preparation of such systems.

STATE OF THE ART

In regenerative medicine, synthetic implants are required to act as three-dimensional scaffolds guiding tissue growth. Polyesters are a group of biodegradable polymers widely used to build scaffolds among other biomedical applications. Poly(epsilon-caprolactone) (PCL) and poly(D,L-lactic-co-glycolic) acid (PLGA) are particularly common, belong to FDA-approved products and break down into oligomers and monomers by hydrolysis of their ester bonds in the aqueous medium of the organism. The physical and mechanical properties and degradation resistance of these polymers can be adjusted by regulating the monomer ratio, molecular weight, and degree of crystallinity (Makadia H K, Siegel S I, *Poly-lactic-co-glycolic acid (PLGA) as biodegradable controlled drug delivery carrier. Polym* 3, 1377-1397, 2011). The use of PLGA of low inherent viscosity is particularly suitable for the regeneration of bone tissue since the degradation time is between 8 to 10 weeks. On the other hand, the complete degradation of PCL requires times greater than 24 months, being one of the preferred polymers for the development of implantable systems for prolonged release of drugs (Dash T. K., Konkimalla V. B. *Poly(-e-caprolactone) based formulations for drug delivery and tissue engineering: A review. J. Controlled Release,* 2012, 158, 15-33). Compared to other biodegradable polymers, PCL has greater strength and elasticity, being of choice in the manufacture of scaffolds for regeneration of tissues exposed to moderate mechanical stress such as tendon, cartilage, and bone (Abedalwafa M Wang F, Li C. *Biodegradable poly-epsilon-caprolactone (PCL) for tissue engineering applications: A review. Rev. Adv. Mater. Sci,* 2013, 34, 123-140).

On the other hand, the sterilization of these scaffolds is essential for their safe use in vivo, in order to avoid post-surgical complications linked to infections in the area implanted with the scaffold. The current legal framework dictates that the sterilization method to be used must comply with SAL-6 sterility levels against endospores before use (Rutala W. A., Weber D. J., and the *Healthcare Infection Control Practices Advisory Committee. "Guideline for Disinfection and Sterilization in Healthcare Facilities,* 2008" Centers for Disease Control and Prevention. 2008); (*ISO* 14937:2009 *Sterilization of health care products—General requirements for characterization of a sterilizing agent and the development, validation, and routine control of a sterilization process for medical devices. International Organization for Standardization,* 2009). SAL-6 is defined as a probability of $10^{-6}$, i.e., one in a million, of viable microorganisms being present in the product after sterilization treatment. Bioindicators are required to confirm that these SAL-6 levels are reached, with bacterial endospores being the most common choice of bioindicators due to their high resistance to sterilization.

There is no single sterilization process suitable for the sterilization of any type of medical device or biological tissue. In fact, many new generation medical devices cannot reach the market due to the lack of adequate sterilization treatment for them. In addition, conventional sterilization treatments (heat/steam, ethylene oxide and gamma sterilization) are inefficient against biological tissues and numerous synthetic materials for biomedical use, particularly in medical devices with polymeric components, due to the high temperatures used, physicochemical changes associated with radiation techniques and/or the insufficient penetration capacity of the technique (White A, Burns D, Christensen T W, *Effective terminal sterilization using supercritical carbon dioxide. J Biotechnol.* 2006, 123 (4), 504-15).

Technological approaches have been reported for the processing of porous scaffolds by foaming with compressed gases or supercritical fluids and for the sterilization with supercritical fluids of materials that maintain their physical integrity after such treatment. However, it is technically very difficult to achieve polymeric scaffolds of polyesters by means of foaming with compressed gases or supercritical fluids that are sterile. Compressed gases or supercritical fluids in general, and carbon dioxide ($CO_2$) in particular, are used as plasticizing agents in the process known as compressed $CO_2$-assisted foaming or supercritical foaming for the production of polymeric scaffolds without the use of solvents. The range of biopolymers susceptible to be processed by this technique is wide and predominantly with polymers of medium and high molecular weight, recently being extended to polymers of low molecular weight (inherent viscosity below 0.5 dL/g) (Diaz-Gómez L, Yang F, Jansen J. A, Concheiro A, Alvarez-Lorenzo C, Garcia-González C A. *Low viscosity-PLGA scaffolds by compressed $CO_2$ foaming for growth factor delivery. RSC Adv,* 2016, 6, 70510-70519).

Supercritical carbon dioxide ($scCO_2$) is recognized as a sterilizing agent capable of inactivating vegetative forms and, to a lesser extent, endospores, of viruses and Gram-positive and Gram-negative bacteria preferably in suspension rather than freeze-dried forms (Ribeiro N, Soares G C, Santos-Rosales V, Concheiro A, Alvarez-Lorenzo C, Garcia-González C A, Oliveira A L, *A new era for sterilization based on supercritical $CO_2$ technology, J BiomedMater Res.* 2020, 108(2), 399-428); (Soares G C, Learmonth D A, Vallejo M C, Davila S P, González P, Sousa R A, et al. *Supercritical $CO_2$ technology: The next standard sterilization technique? Mater Sci Eng C.* 2019, 99:520-40). The use of this type of treatment has been proposed for the sterilization of thermosensitive materials such as biopolymers, materials sensitive to degradation by hydrolysis, food products, biological implantation tissues, drugs, drug delivery systems and medical devices without impacting on the integrity of the material and on the properties of the material after treatment (U.S. Pat. No. 6,149,864A, US20070003432A1, EP1782839A1, US20090 041620A1, EP1782839A1, US20040120852, US20140193552A1). This sterilization capacity of supercritical $CO_2$ is not reproducible using other supercritical fluids such as tetrafluoroethane or another compressed fluid such as nitrogen (U.S. Pat. No. 6,149,864 A), except in the case of nitrogen oxide (WO2019168428A1). The main operating variables are temperature and pressure. The temperature must be as moderate as possible so as not to damage the components of the material to be sterilized, but without compromising the efficiency of the sterilization process, values in the range of 25 to 135° C. being suggested. The pressure is selected based on the process temperature inversely and usually in the range of 69 to 276 bar. The use of agitation, pressure cycles or rapid depressurization to atmospheric pressure or vacuum can also facilitate the sterilization process. The incorporation of additives, such as hydrogen peroxide, ethanol, peracetic acid, acetic acid and mixtures of these in proportions of 0.001 to 2.0% by volume with respect to the volume of the sterilization autoclave extends the possibility of inactivation of bacteria in the form of endospores to SAL-2 levels and higher by supercritical treatment (Ribeiro N, Soares G C, Santos-Rosales V, Concheiro A, Alvarez-Lorenzo C, Garcia-González C A, Oliveira A L. *A new era for sterilization based on supercritical $CO_2$ technology, J Biomed Mater Res.* 2020, 108(2), 399-428); (Dai Z, Ronholm J, Tian Y, Sethi B, Cao X *Sterilization techniques for biodegradable scaffolds in tissue engineering applications. J Tissue Eng.* 2016, 7, 204173141664881). The residual presence of these additives in the treated materials can cause toxicity or discomfort problems, which is why very low additive contents are used (less than 200 ppm of hydrogen peroxide) or, more frequently, aeration or extraction post-processing is carried out to eliminate these residues (US20100080790A1). The presence of water also increases the sterilization capacity of supercritical $CO_2$. The moderate temperature conditions and excellent permeability of $scCO_2$ make the use of this treatment attractive for biomaterials in general and for porous biomaterials in particular. Furthermore, this sterilization technique is able to preserve the physicochemical properties of the material for certain thermosensitive polymeric scaffolds used in regenerative medicine (Bernhardt A, Wehrl M, Paul B, Hochmuth T, Schumacher M, et al. *Improved Sterilization of Sensitive Biomaterials with Supercritical Carbon Dioxide at Low Temperature. PLOS ON.* 2015, 10 (6): e0129205); (Lanzalaco S, Campora S, Brucato V, Carfì Pavia F, Di Leonardo E R, Ghersi G, et al. *Sterilization of macroscopic poly(l-lactic acid) porous scaffolds with dense carbon dioxide: Investigation of the spatial penetration of the treatment and of its effect on the properties of the matrix. J Supercrit Fluids.* 2016, 111:83 90); (Scognamiglio F, Blanchy M Borgogna M Travan A, Donati I, Bosmans J W A M, et al. *Effects of supercritical carbon dioxide sterilization on polysaccharidic membranes for surgical applications. Carbohydr Polym.* 2017, 173:482-8); (Ruphuy G, Souto-Lopes M Paiva D, Costa P, Rodrigues A E, Monteiro F J, et al. *Supercritical $CO_2$ assisted process for the production of high-purity and sterile nano-hydroxyapatite/chitosan hybrid scaffolds. J Biomed Mater Res B Appl Biomater.* 2018, 106(3):965-75). SAL-6 levels with *B. pumilus* as a bioindicator after supercritical sterilization have only been described for temperatures equal to or greater than 60° C., addition of hydrogen peroxide (200 ppm) and pressures of 276 bar (US20100080790A1).

However, obtaining scaffolds of PCL, PLGA, particularly PLGA of low inherent viscosity, from mixtures of these, or other compositions containing at least one of these two components treated by supercritical sterilization is difficult due to the plasticizing effect of $CO_2$ under the usual conditions of supercritical sterilization. Under these conditions, the use of the thermoplastic polymers mentioned above in medical devices is highly restricted due to very significant morphological and internal structure changes after sterilization treatment that result in products of low quality or that do not fulfill the function that they are intended for.

Thus, there is still a need to provide porous matrices based on PCL, PLGA of low inherent viscosity, mixtures of these, or other compositions containing at least one of these two components, and which are sterile and with modulable external morphology. Furthermore, there is also a need for supercritical $CO_2$ sterilization treatment of medical devices, drugs, foodstuffs, implantable biological tissues, or components thereof, that are more efficient in terms of processing time and capable of integrating the removal of additives from sterilization during such treatment without the need for post-processing.

BRIEF DESCRIPTION OF THE INVENTION

The present invention is directed to a sterilization process that allows obtaining more controlled results of the final sterilized product. More specifically, it is directed to a sterilization procedure through the integration of foaming, molding, and sterilization processes, all of them assisted by a compressed gas or supercritical fluid. Even more specifically, sterilization takes place in the presence of a compressed gas or a supercritical fluid in a discontinuous stage, another with continuous flow of a compressed gas or a supercritical fluid, and a final depressurization stage.

Thus, in a first aspect, the invention relates to a sterilization process, comprising:

a) introducing the material to be sterilized inside an autoclave, and a sterilization additive in concentrations of between 100 and 3000 ppm;

b) heating the system to a temperature equal to or less than 80° C.;

c) introducing a compressed gas or supercritical fluid into the autoclave at a pressure of between 40 and 300 bar and at a temperature of between 20 and 80° C. and maintaining these pressure and temperature conditions for between 5 minutes and 24 hours;

d) passing a continuous flow of $CO_2$ of from 2 to 500 g/min through the autoclave which is maintained at a pressure of between 40 and 300 bar and at a temperature of between 20 and 80° C., for between 5 minutes and 24 hours; and e) depressurizing to atmospheric pressure.

Thus, the process of the invention makes it possible obtaining a medical device, drug, cosmetic or food product or components thereof in sterile conditions.

Furthermore, the method of the invention is especially suitable for preparing a sterile porous matrix comprising poly(D,L-lactic-co-glycolic) acid, and/or poly(epsilon-caprolactone), and which is homogeneous, of solid or semi-solid consistency and with a porosity greater than 60%.

In a particular embodiment, the procedure described above is directed to obtaining a sterile, homogeneous porous matrix, of solid or semi-solid consistency, of a porosity greater than 60%, comprising poly(D,L-lactic-co-glycolic) acid and/or poly(epsilon-caprolactone), where the material to be sterilized in step a) is a physical mixture of poly(D, L-lactic-co-glycolic) acid and/or poly(epsilon-caprolactone), provided that the depressurization of step e) is carried out in a controlled manner at a rate of between 1 and 50 bar/min down to atmospheric pressure.

The invention also relates to a process for the preparation of porous matrices incorporating poly(D,L-lactic-co-glycolic) acid of inherent viscosity less than 0.45 dL/g. This polymer is particularly difficult to handle, but the conditions of the procedure described here makes it possible obtaining implants or scaffolds constituted by this polymer. Thus, in a preferred embodiment, when the material to be sterilized in step a) is a physical mixture of poly(D,L-lactic-co-glycolic) acid with an inherent viscosity of less than 0.45 dL/g, or is a physical mixture of poly(D,L-lactic-co-glycolic) acid with an inherent viscosity of less than 0.45 dL/g and poly (epsilon-caprolactone), the procedure further comprises:

a step d') after step d) and prior to step e), which comprises passing a continuous flow of liquid $CO_2$ at a temperature of 4° C. or less, of from 2 to 500 g/min through the autoclave maintained at a pressure of between 40 and 300 bar, for between 5 minutes and 24 hours, and a step e') replacing step (e), comprising a controlled depressurization at a rate of between 1 and 19.5 bar/min with cooling by the addition of a compressed liquid, which is gaseous at 25° C. and at a pressure of 1 atmosphere, at a temperature of from −196° to 19° C., down to atmospheric pressure.

In a particular embodiment, the addition of the compressed liquid in step e') is continuous or discontinuous.

In addition, porous matrices, implants, or scaffolds obtained by the process of the invention have characteristics that are particularly suitable for the regeneration of bone and cartilaginous tissue. Said matrices, implants or scaffolds are biodegradable, porous, homogeneous, of solid or semisolid consistency and modulable external morphology, characteristics that make it particularly suitable for regenerative medicine.

Thus, a second aspect of the invention is directed to an implant or scaffold obtainable according to the process of the first aspect of the invention.

A third aspect of the invention is directed to the use of the implant or the scaffold of the invention, for the manufacture of a drug. In a particular embodiment, the invention is directed to scaffolds and implants as described above, for use as a drug. In another particular embodiment, the drug is for the treatment of pathological or physiological states in humans or animals. In a more particular embodiment, the drug is for bone regeneration. In another particular embodiment, the drug is for regeneration of cartilage. In another aspect, the invention is directed to the use of the system as defined above for the preparation of scaffolds for regenerative medicine and tissue engineering.

The scaffold according to the invention is suitable as a monolithic implant, for controlled release of biologically active substances at the site of application. In a particular embodiment, the systems of the invention, implants and scaffolds as described above, are part of a monolithic implant. In a particular embodiment, the system of the invention can be obtained as a monolithic implant for controlled release at the site of application without toxic effects.

DESCRIPTION OF THE FIGURES

FIG. 2. Photographic images and SEM of scaffolds of a) PCL containing Rhodamine B in the ratio PCL:Rhodamine B 99.5:0.5 w/w, b) PCL containing vancomycin hydrochloride in the ratio PCL:vancomycin 95:5 w/w, c) PCL containing pre-gelled starch and vancomycin hydrochloride in a ratio PCL:starch:vancomycin 85:10:5 by weight, with supercritical $CO_2$ at 39° C., 140 bar and addition of 1200 ppm hydrogen peroxide during discontinuous stages and continuous compressed $CO_2$ flow for 2.5 and 2.5 hours, respectively. Scale bars: 5 mm (black), 100 μm (white).

Figure 3:
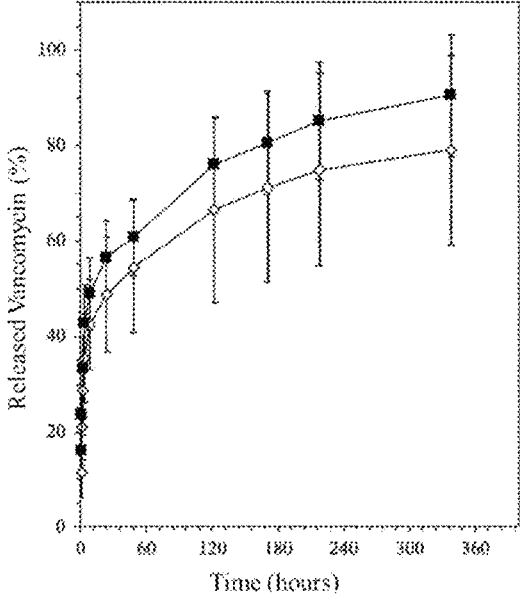
Figure 3:
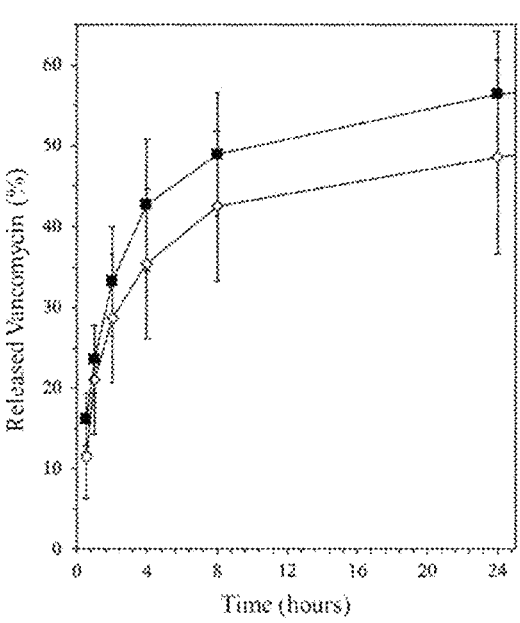

FIG. 3. Vancomycin hydrochloride release profiles (PBS medium pH 7.4, 37° C., 60 rpm) corresponding to scaffolds of i) PCL containing vancomycin hydrochloride in a ratio PCL:vancomycin 95:5 w/w, ii) PCL containing pre-gelled starch and vancomycin hydrochloride in a ratio PCL:starch: vancomycin 85:10:5 by weight, after addition 1200 ppm hydrogen peroxide and supercritical $CO_2$ processing at 39° C., 140 bar during discontinuous stages and continuous compressed $CO_2$ flow for 2.5 and 2.5 hours, respectively. Legend: PCL:vancomycin 95:5 w/w (white rhombus), PCL: starch:vancomycin 85:10:5 p/w (black square).

Figure 4:
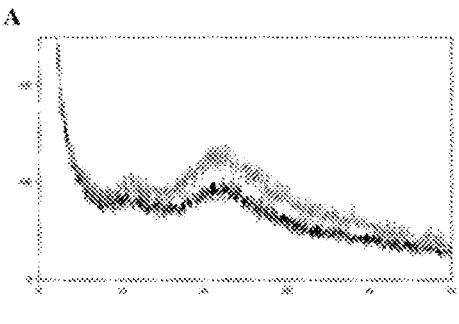
Figure 4:
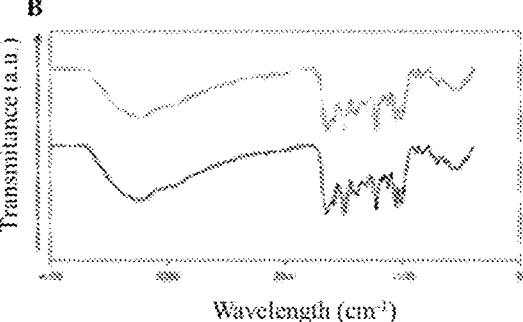

FIG. 4. X-ray diffraction spectrum (A) and infrared spectrum (B) of vancomycin hydrochloride i) untreated and (ii) after addition of 1200 ppm hydrogen peroxide and processing with supercritical $CO_2$ at 39° C., 140 bar during batch stages and continuous compressed $CO_2$ flux for 2.5 and 2.5 hours, respectively. Caption: vancomycin untreated hydrochloride (black), vancomycin treated hydrochloride (gray)

Figure 5:
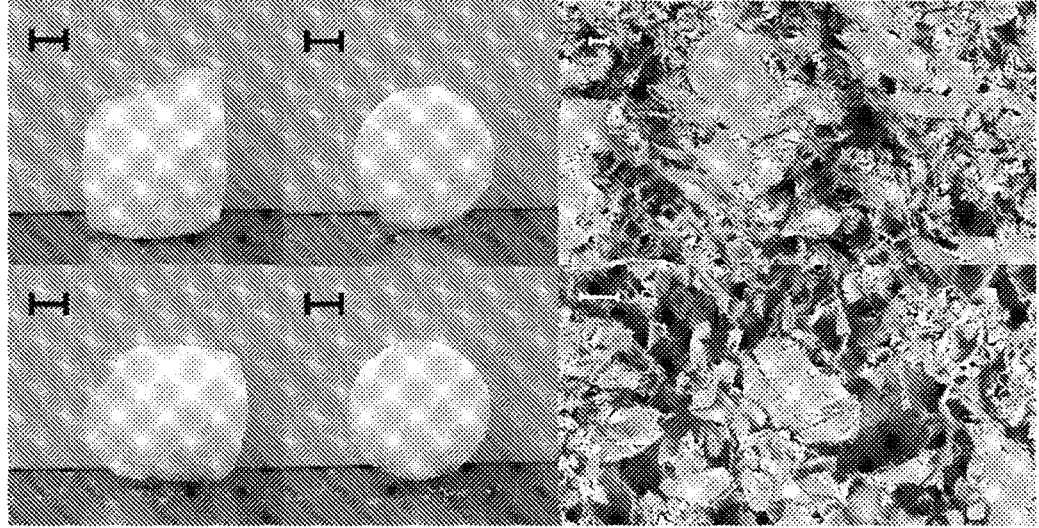

FIG. 5. Photographic and SEM images of a powdery mixture of PCL and PLGA with a weight ratio 50:50, after integrated treatment of foaming and sterilization according to the conditions of example 4. Scale bars: 5 mm (black), 100 μm (white).

Figure 6:
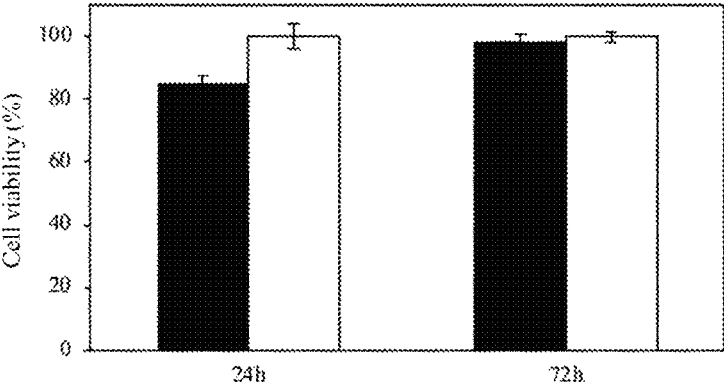

FIG. 6. Cell viability results (WST-8 test) of fibroblasts after 24 and 72 hours in contact with the sterile material obtained according to the conditions of example 4. The material was incubated with the cells without previous aeration steps. Legend: PCL/PLGA scaffold obtained according to the conditions of example 4 (black), negative control: cells incubated without the presence of the material (white).

Figure 7:
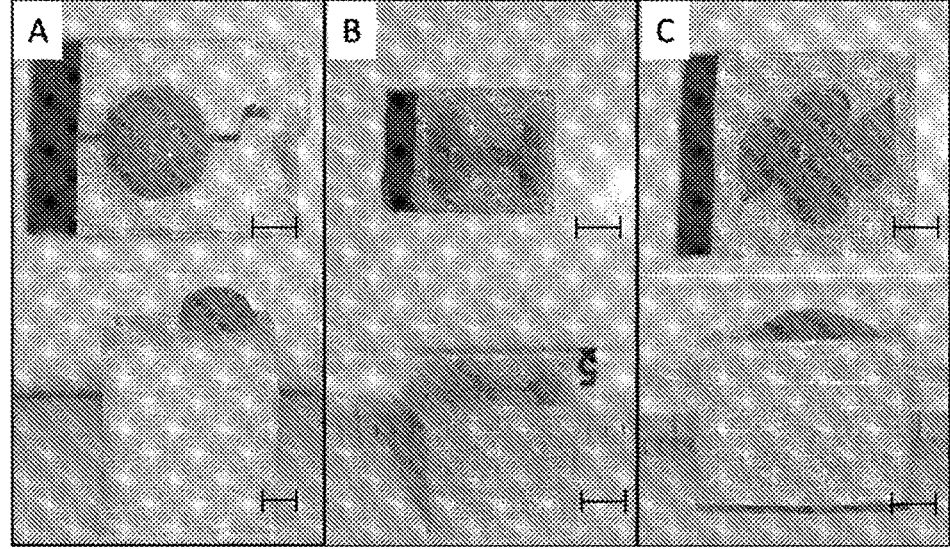

FIG. 7. Photographic images of PCL and Rhodamine B scaffolds in a PCL:Rhodamine B ratio 99.5:0.5 w/w, after integrated foaming treatment and sterilization in customized PLLA molds of different dimensions according to the conditions of example 8. Scale bar: 0.5 mm.

Figure 8:
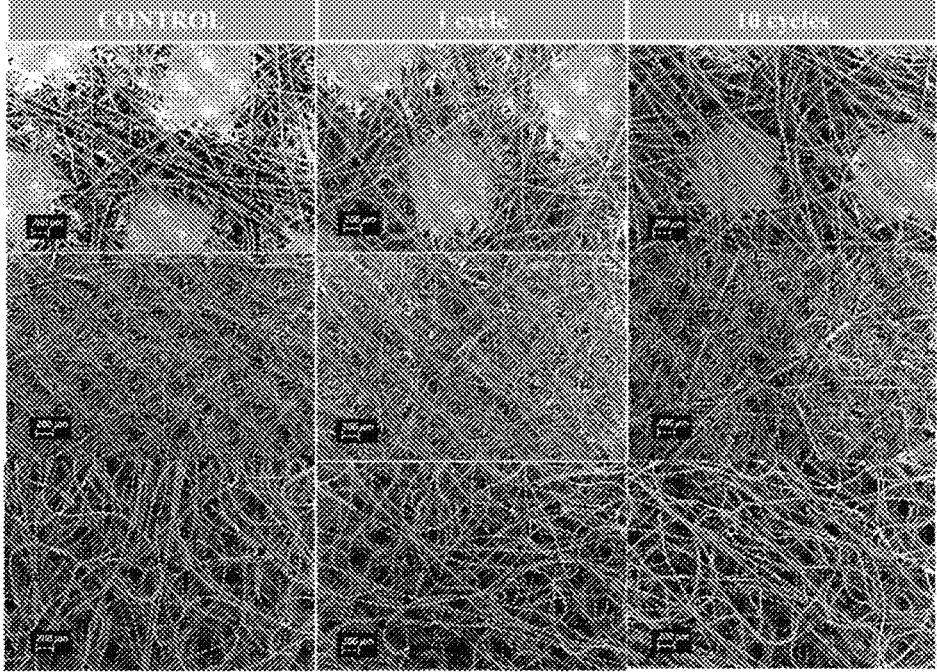

FIG. 8. Electron microscopy (SEM) images of the different layers in terms of composition (external; polypropylene spunbond fabric, intermediate; cotton, internal; polypropylene cast fabric) of an FFP3 mask.

DETAILED DESCRIPTION OF THE INVENTION

As discussed above, the invention relates to a sterilization process, which comprises:

a) introducing the material to be sterilized inside an autoclave, and a sterilization additive in concentrations of between 100 and 3000 ppm;

b) heating the system to a temperature equal to or less than 80° C.;

c) introducing a compressed gas or supercritical fluid into the autoclave at a pressure of between 40 and 300 bar and at a temperature of between 20 and 80° C. and maintaining these pressure and temperature conditions for between 5 minutes and 24 hours;

d) passing a continuous flow of $CO_2$ of from 2 to 500 g/min through the autoclave which is maintained at a pressure of between 40 and 300 bar and at a temperature of between 20 and 80° C., for between 5 minutes and 24 hours; and

Thus, the process of the invention makes it possible sterilizing a material under suitable conditions to have a sterile system.

The process to which the invention relates has the advantages that it requires the incorporation of low contents of sterilizing agents and that it allows their elimination before the conclusion of the process without post-processing steps, is carried out in a single step, speeds up the sterilization process and the working temperatures are of between 20 and 40° C. which are compatible with the incorporation of thermosensitive components such as biologically active substances, it also takes place in environmentally friendly conditions, and overcomes the current limitations of the use of polymers that lose their physical integrity after processing and particularly biopolymers of low inherent viscosity such as PLGA of inherent viscosity less than 0.45 dL/g.

In addition, the process to which the invention refers provides products in sterile conditions through the use of supercritical fluid with additives and reduces sterilization times compared to discontinuous $CO_2$ sterilization processes under the same conditions of pressure, temperature, and additive content.

The term "sterile system" refers to a material that meets the SAL-6 sterility requirement after sterilization treatment against the bioindicators *Bacillus stearothermophilus, Bacillus subtilis* and/or *Bacillus pumilus.*

The term "sterile conditions" refers to SAL-2 or higher sterility conditions after sterilization treatment against the bioindicators *Bacillus stearorthermophilus, Bacillus subtilis* and/or *Bacillus pumilus.*

In a preferred embodiment, the sterilization additive is hydrogen peroxide in proportions of 1200 to 3000 ppm to reach SAL-6 levels.

In a preferred embodiment, the sterilization additive is hydrogen peroxide in proportions of 600 to 1200 ppm to reach SAL-4 levels.

In a preferred embodiment, the sterilization additive is hydrogen peroxide in proportions of 100 to 600 ppm to achieve SAL-2 levels.

According to step a) of the procedure, the material to be sterilized is introduced inside the autoclave or can be introduced into a pressure vessel used for this purpose, together with the sterilization additives. The introduction of the sterilization additives, according to step a) of the procedure, can be carried out, for example, by depositing it either directly at the bottom of the autoclave, or with a gauze or compress previously impregnated with the additive before closing the autoclave, or through a specific inlet line to the autoclave once closed and subjected to vacuum or atmospheric pressure. Preferably, there is no physical contact between the sterilization additive and the material to be processed in this step a). Alternatively, the additive can be introduced into the autoclave already closed and under pressure.

In this procedure, the material of stage a) may retain its physical integrity until the end of the process, or it may lose its physical integrity and thereby the material of step a) has a different physical form than the sterile system obtained.

PLGA is a biodegradable synthetic polymer of the family of aliphatic polyesters, in particular, it is an alpha-hydroxy acid copolymer of polylactic acid and polyglycolic acid. In the present invention PLGA also includes copolymers of polylactic acid and poly glycolic acid with a terminal group selected from hydroxy, carboxyl and ester. The PLGA of the invention has a lactic:glycolic ratio of between 85:15 to 40:60, preferably between 75:25 to 50:50.

The present invention also relates to a process for obtaining a porous, sterile, homogeneous matrix, of solid or semi-solid consistency, porosity greater than 60%, said matrix comprising PCL and/or PLGA. Due to the very nature of these polymers, the matrix obtained is also biodegradable.

Figure 1:
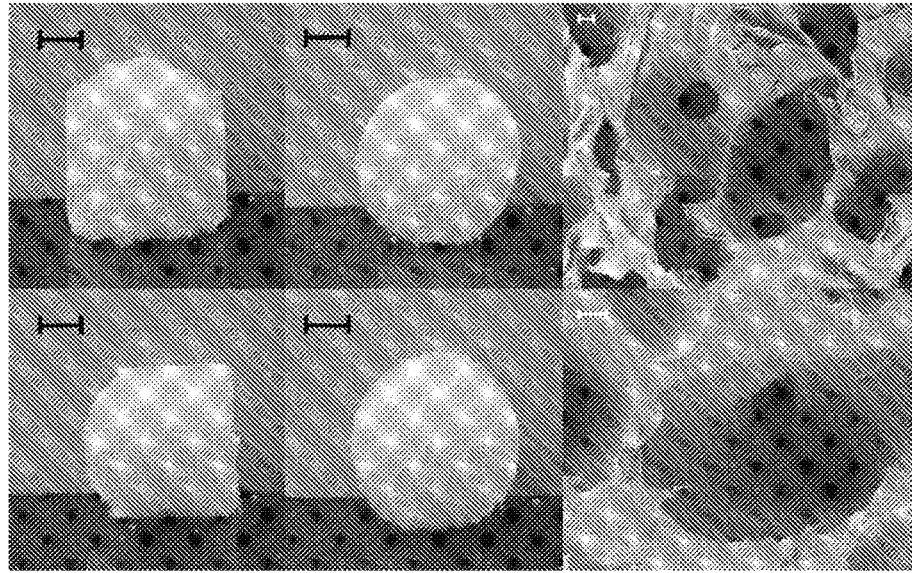
FIG. 1. Photographic and SEM images of PCL scaffolds processed with supercritical $CO_2$ at 39° C., 140 bar and addition of 1200 ppm hydrogen peroxide during discontinuous stages and continuous compressed $CO_2$ flow for a) 5 and 0 hours, b) 2.5 and 2.5 hours and c) 0 and 5 hours, respectively. Scale bars: 5 mm (black), 100 μm (white).
Figure 1:
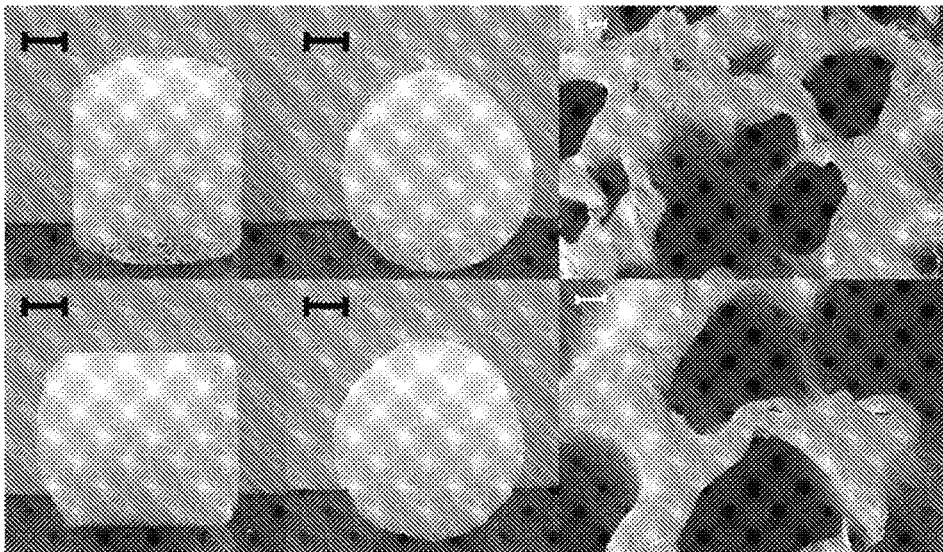
Figure 1:
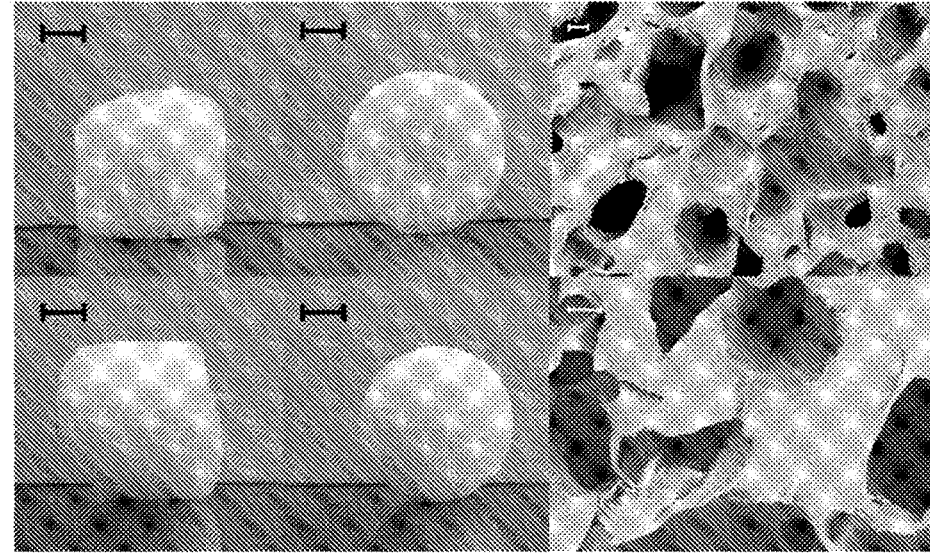
Figure 2:
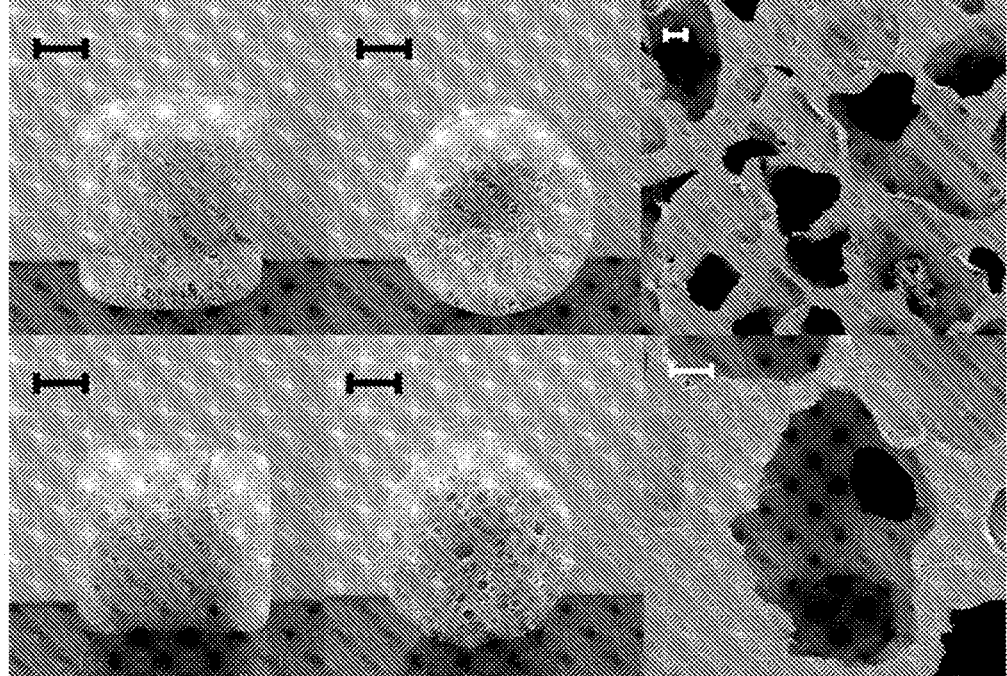
Figure 2:
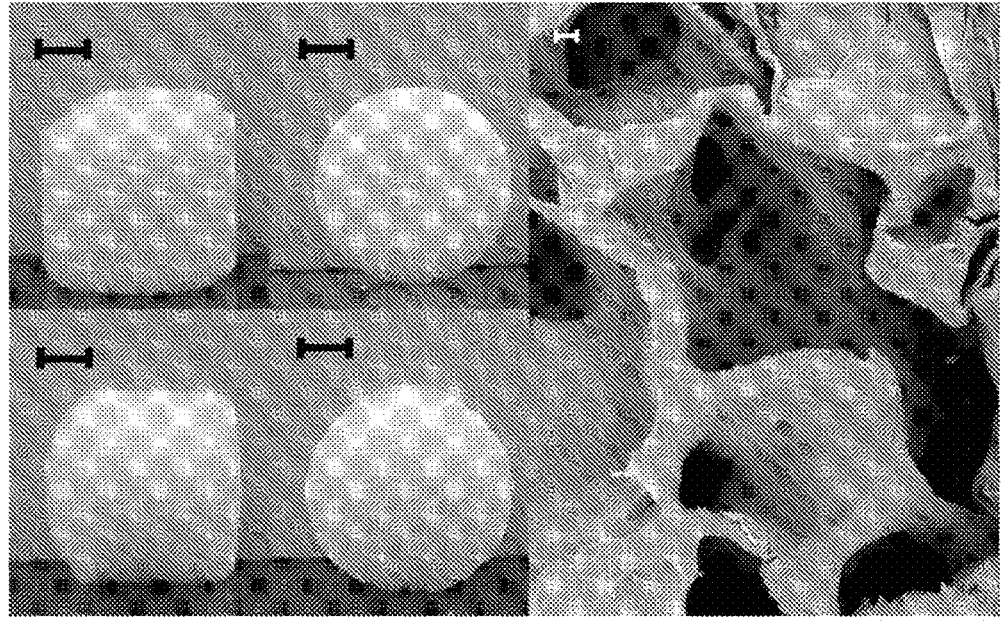
Figure 2:
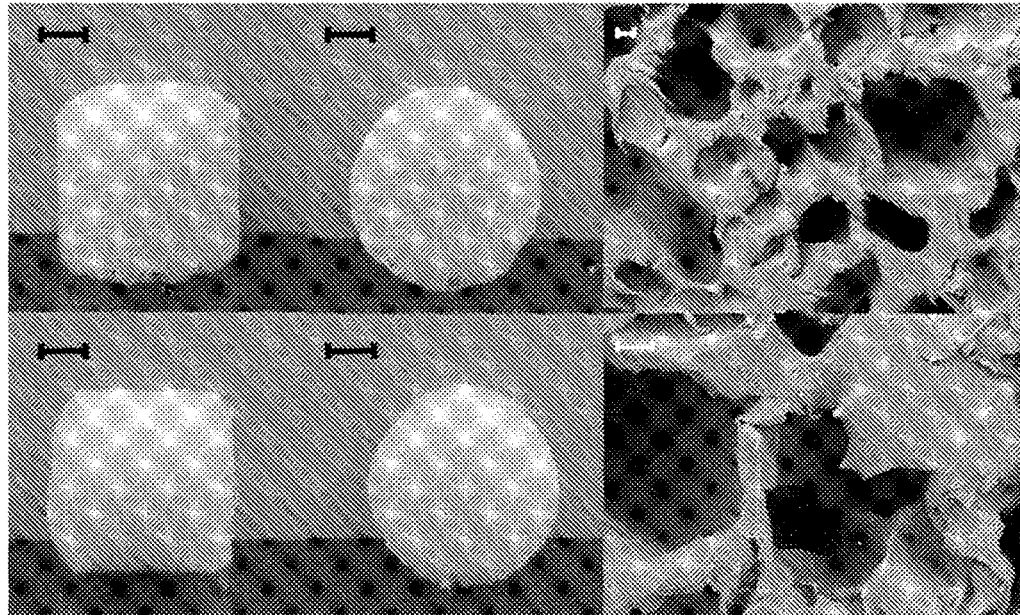

The expression "homogeneous matrix" refers to a matrix with spatial uniformity in its internal structure and uniformity in its composition. In the homogeneous matrix, obtained by the process of the invention, there are no traces of the powdery morphologies typical of the starting materials as demonstrated in the examples and in particular in examples 2 and 3 and FIGS. 1 and 2.

When polymers poly(D,L-lactic-co-glycolic), and/or poly (epsilon-caprolactone) are used as a starting material in step a), these polymers are found as a physical mixture. This physical mixture loses its integrity throughout the procedure and as a result undergoes structural changes, whereby the procedure makes it possible obtaining a porous, sterile, homogeneous matrix, of solid or semisolid consistency, of porosity greater than 60%, which is constituted by poly(D, L-lactic-co-glycolic) acid and/or poly(epsilon-caprolactone). For this, the depressurization of step e) must be carried out at a controlled rate of between 1 and 50 bar/min down to atmospheric pressure.

PLGA with inherent viscosity of less than 0.45 dL/g degrades at a more suitable rate than other types of PLGA for bone or cartilage regeneration. For this reason, the preferred type of PLGA of the present invention is PLGA having an inherent viscosity of less than 0.45 dL/g.

"Inherent viscosity" refers to the measurement of the flow time of a polymer solution, usually at 0.1% w/w in chloroform at 25° C., through a narrow capillary relative to the flow time of the pure solvent through the same capillary and expressed per unit of polymer concentration. It is a rheological method for determining the molecular weight of a polymer and is generally expressed in units of deciliters per gram.

Thus, when the material to be sterilized in step a) is a physical mixture of poly(D,L-lactic-co-glycolic) acid with an inherent viscosity of less than 0.45 dL/g, or is a physical mixture of poly(D,L-lactic-co-glycolic) acid with an inherent viscosity of less than 0.45 dL/g and poly(epsilon-caprolactone), the procedure further includes:

a step d') after step d) and prior to step e), comprising passing a continuous flow of liquid $CO_2$ at a temperature of 4° C. or less, of from 2 to 500 g/min through the autoclave maintained at a pressure of between 40 and 300 bar, for between 5 minutes and 24 hours, and a step e') replacing step (e), comprising controlled depressurization at a rate of between 1 and 19.5 bar/min with cooling by the addition of a compressed liquid, which is gaseous at 25° C. and 1 atmosphere of pressure, at a temperature of between −196° and 19° C., down to atmospheric pressure.

Steps d') and e') are particularly designed for obtaining systems that comprise a matrix based on PLGA with low inherent viscosity, in particular an inherent viscosity of less than 0.45 dL/g, since it avoids the problems found in the technique for this material without control over its external and internal morphology, with pores of several millimeters and which loses its mechanical integrity making it useless for its purpose as an implant or scaffold.

The invention has the advantage of processing a physical mixture of the polymers mentioned in a single stage, to obtain a matrix as defined above, and also sterilizing it in the same process. Therefore, it is not necessary to have a porous matrix in advance and to sterilize it at a later stage, instead the process of preparation of the porous matrix and its sterilization take place in a single process.

The term "physical mixture" refers to a powder material which can optionally be mixed with other powder materials by standard mixing techniques, such as a paddle mixer, a planetary mixer, or a turbula-type mixer.

In addition, this physical mixture can be poured into a mold. An additional advantage of the invention is that the method makes it possible obtaining matrices with modulable external morphology. The expression "modulable external morphology" refers to the fact that the size and external shape are adaptable to specific requirements, for example they adapt their shape to that of a mold. Thereby, by including a mold in step a) of the procedure, the external morphology of the final material can be modulated in terms of its dimensions and shape, so that the material will acquire the morphology of the negative of the mold that contains it.

In a particular embodiment, step a) of the procedure includes a mold, preferably when the material to be sterilized is a physical mixture of poly(D,L-lactic-co-glycolic) acid and/or poly(epsilon-caprolactone) it is poured into a mold in step a).

In a preferred embodiment, in step a) of the process of the invention a biologically active substance is additionally added. In a particular embodiment, this biologically active substance is part of the physical mixture of the materials of step a).

The term "biologically active substance" refers to any substance that modifies, promotes, accelerates, prolongs, inhibits, activates, or at least affects biological or chemical processes taking place in humans and animals. When one or more biologically active substances are incorporated into the system of the invention, they are dispersed at the molecular or at the particle level. The system is suitable for incorporating biologically active substances regardless of their solubility characteristics. Due to the characteristics of the components of the system and the processing conditions, the system is particularly suitable for incorporating thermosensitive biologically active substances.

In a particular embodiment, biologically active substances are selected from hormones, anti-inflammatories, antineoplastics, antimicrobial agents and morphogenic substances for repairing bone defects and other applications in regenerative medicine. In a more particular embodiment, the biologically active substance is an antibiotic. This preparation is intended for surgical infections during implantation in soft tissues and bones.

In another particular embodiment, the proportion of biologically active substance is between 0.1% and 15% by weight with respect to PLGA, PCL or a mixture of both or of at least one of these two biopolymers.

In a particular embodiment, the temperature used in steps b), c) and d) is equal to or less than 40° C., to facilitate the processing of thermosensitive materials, for example biologically active molecules. A temperature regulator can make it possible to set the desired initial sterilization temperature in the autoclave, thereby facilitating the execution of steps b), c) and d) of the procedure.

The autoclave is pressurized to the desired pressure by adding a compressed gas or supercritical fluid under pressure, according to step c) of the procedure, e.g., through a liquid pump or a compressor. Alternatively, but not preferably, the introduction of the supercritical fluid into the aforementioned autoclave can be carried out in liquid or solid state.

In a preferred embodiment, in step c) the supercritical fluid or compressed gas is selected from carbon dioxide, nitrous oxide or a mixture thereof with nitrogen, ethanol or isopropanol. This gas is introduced into the autoclave discontinuously, i.e., once the desired pressure has been reached at the operating temperature, it is not necessary to continue introducing the gas. In this way, step c) makes it possible bringing the material to be sterilized in contact with the sterilization additive introduced in step a), with the supercritical fluid or the compressed gas of choice.

The pressurization rate of the autoclave is not a critical parameter for this process. The process of attaining the desired temperature and pressure can be carried out either sequentially or simultaneously. In a particular embodiment, the contact time between the compressed gas or supercritical fluid and the mixture is of between 5 minutes and 24 hours. In a more particular embodiment, it is of between 15 minutes and 6 hours. In a preferred embodiment, it is of between 1 and 5 hours.

The present invention uses a processing medium under compressed gas or supercritical fluid conditions. A fluid is in supercritical conditions when its pressure and temperature are above those of its critical point and is characterized by properties intermediate between those of a liquid and a gas. Examples of fluids that may be used with this invention are selected from carbon dioxide ($CO_2$), nitrous oxide or a mixture thereof with nitrogen, ethanol, or isopropanol. The present invention contemplates the use of these substances separately or in combination, as well as the use of additives. In a particular embodiment of the invention, the compressed gas or supercritical fluid is $CO_2$. The individual use of $CO_2$ as a processing medium is preferred due to its plasticizing, sterilizing and foaming capacity, its non-flammability, low cost, and its easy removal from the medium at ambient temperature and pressure. There will therefore be no residual $CO_2$ in the final product that could contribute to problems in its use.

The term "supercritical carbon dioxide" refers to carbon dioxide in the ranges of temperature and pressure conditions mentioned above, pressure between 40 and 300 bar and at a temperature of between 20 and 80° C., which are satisfactory in the present invention.

In step d), a continuous flow of carbon dioxide at a pressure of between 40 and 300 bar, accelerates the sterilization process, and gradually removes the sterilization additive to residual levels in the treated material.

The sequence of steps c) and d) is beneficial for sterilization of the material to take place and also for removing the remains of the sterilization additive. If step c) were eliminated, there would be a premature and accelerated elimination of the sterilization additive, and the process would not ensure sterilization of the material. In a preferred embodiment, stages c) and d) take place with agitation.

A continuous flow of pressurized carbon dioxide, according to step d) of the procedure, accelerates the sterilization process. This flow can be supplied, for example, by the addition of pressurized carbon dioxide, through a liquid pump or a compressor and controlled by a micrometric valve or a manual or automatic backpressure control system with electronic control loop.

The carbon dioxide used in the present invention is substantially pure, although the presence of other gases is tolerated, unless they limit the sterilization, foaming or plasticizing capacity of the carbon dioxide.

In a preferred embodiment, step d) takes place with a flow of between 2 and 50 g/min. This step serves to gradually eliminate the sterilization additive to residual levels in the treated material. This flow was calculated for a sterilization autoclave of 100 mL at 2L capacity. An expert in the field is able to increase this flow rate for higher autoclave volumes, so as to obtain carbon dioxide average residence times similar to those de scribed above.

In the case of PLGA of inherent viscosity less than 0.45 dL/g, the transition between step d) and step d') is made by reducing the temperature by applying a continuous flow of liquid carbon dioxide. In a particular embodiment, the temperature of the mixture inside the autoclave is between 10° C. and 50° C., more particularly between 15° C. and 45° C.

In a particular embodiment, continuous step d') is not necessary to obtain porous scaffolds under sterile conditions from mixtures of PLGA with an inherent viscosity less than 0.45 dL/g and PCL from a PCL:PLGA weight ratio of 50:50 w/w or higher proportion of PCL.

In another particular embodiment, the proportion of PLGA or PCL is between 50% and 99.9%.

The compressed gas or supercritical fluid in step c), and carbon dioxide in step d), interact with polymers acting as plasticizer and swelling agent, thereby reducing the vitreous transition temperature and/or the melting temperature in the event that a biodegradable synthetic polyester is present in the mixture. The amount of fluid absorbed during processing and the consequent swelling of the polymeric mixture is proportional to the temperature and pressure of the processing medium.

The mixture of step e) can be depressurized and cooled sequentially or simultaneously to obtain the sterile system with solid or semi-solid consistency and homogeneous appearance. When cooling sequentially, this occurs once atmospheric pressure is reached, while when cooling simultaneously, temperature reduction is initiated during depressurization. During the removal of carbon dioxide, thermodynamic instability occurs leading to the formation of hollow volume (porosity) by nucleation. As carbon dioxide leaves the matrix, the melting or glass transition temperature rises above the working temperature and the scaffold vitrifies.

During depressurization, according to step e) or e'), down to atmospheric pressure, the rate of degassing or depressurization influences the pore size and interconnectivity of the final scaffold. The cooling rate during depressurization also influences the pore size and interconnectivity of the final scaffold.

In a preferred embodiment, the depressurization rate of step e) is carried out in a controlled manner in the range of 1 to 50 bar/min, more preferably in the range of 3 to bar/min, for example by a micrometric valve or a backpressure system of manual or automatic control by electronic control loop.

The resistance to pore expansion after nucleation is very low for polymeric matrices with components of low inherent viscosity (<0.45 dL/g), forming very large pores (greater than one millimeter). In a particular embodiment, after partial depressurization, cold compressed liquid is added. This makes it possible cooling the material and thus reducing the viscosity of the mixture by lowering the temperature and containing the expansion of the pores. Said compressed liquid must be gaseous at ambient pressure and temperature. The addition of the compressed liquid during step e') is performed either discontinuously in the autoclave once the pressure in the autoclave has been reduced to bar, or continuously in the autoclave with a compressed liquid flow throughout the step. In an embodiment according to the invention, the compressed liquid of step e') is liquid $CO_2$ or liquid $N_2$.

In a particular embodiment, controlled depressurization at stage e') is performed between 1 to 19.5 bar/min, for example by means of a micrometric valve or a backpressure system of manual or automatic control by means of electronic control loop, to have greater control over the pore size distribution of the material. This procedure of the invention is particularly designed to obtain a biodegradable, homogeneous matrix, of solid or semisolid consistency, porosity greater than 60% and an external morphology modulable by the shape and dimensions of the mold used, said matrix comprises PLGA of inherent viscosity less than 0.45 dL/g, or a mixture de PLGA of inherent viscosity less than 0.45 dL/g and PCL.

Putting the process of the invention into practice, sterile systems with a porosity greater than 60% are obtained (see examples 2-5), which is a suitable porosity in implants for bone regeneration. For this, it is favorable to use a matrix with adequate textural properties to facilitate adhesion, penetration, and proliferation of cells, as well as neovascularization and diffusion of gases and nutrients into cells. Thus, it is convenient to use a matrix with porosity analogous to that of trabecular bone of between 50 and 90%, preferably close to its higher value (Karageorgiou V, Kaplan D, *Porosity of 3D biomaterial scaffolds and osteogenesis, Biomater.* 2006, 26, 5474-5491) (Rezvan K, Chen Q Z, B laker J J, Boccaccini A R, *Biodegradable and bioactive porous polymer/inorganic composite scaffolds for bone tissue engineering, Biomater.* 2006, 27, 3413-3431).

As a result of the process of the invention, systems with concave pores are obtained (see examples 2-5). This geometry of the pores is suitable for the application of the systems of the invention to tissue regeneration (Zadpoor A A, *Bone tissue regeneration: the role of scaffold geometry, Biomater. Sci.,* 2015, 3, 231-245).

In a particular embodiment, the invention relates to an additional step to the described process, which comprises the formation of implants: the cooled system can be divided into portions by cutting. In an even more particular embodiment, the removal of a thin, dense, and non-porous outer film may be necessary before being used for implantation purposes.

In a particular embodiment, the procedure as described above further results in the formation of a scaffold such as a monolithic implant. The invention provides a method for processing materials whose physical and mechanical integrity can be modulated under processing conditions until porous materials are obtained by foaming and, optionally, with customized external morphology through the use of molds. The process to which the invention relates is based on the fact that, simultaneously with the sterilization process, the melting or heating of the polymer mixture occurs above the glass transition temperature of PLGA or the melting temperature of PCL, or of the polymer mixture containing PLGA and PCL or of the mixture containing at least one of these two biopolymers in the event that there were additional components as described above.

The systems obtained are suitable as implants capable of providing a release of biologically active substances adjustable to specific requirements.

In another aspect, the invention relates to an implant or scaffold obtainable according to the process of the invention.

In another aspect, relates to the use of the implant of the invention or the scaffold of the invention, for the manufacture of a drug.

In a particular embodiment, the drug is for the treatment of pathological or physiological states in humans or animals.

In a particular embodiment, the drug is for bone regeneration.

In a particular embodiment, the drug is for cartilage regeneration.

In a preferred embodiment, the invention is directed to the use of an implant or scaffold as defined above for the release of biologically active substances, and for the prevention of infections in the implantation region.

incubation (Raypa Digital Incubators) in the absence of agitation and at the recommended incubation temperatures (37° C. for *B. pumilus* and *B. atrophaeus*, and 60° C. for *B. stearothermophilus*). The absence of bacterial growth was further verified by sowing 1 mL of these bacterial suspensions after 7 and 14 days of incubation in tryptone-soybean agar culture medium and counting the microbial colonies formed. The use of a certain time in dynamics with $CO_2$ flow reduced the treatment time to obtain SAL-6 levels against certain species of the genus *Bacillus* (Test #5 and #9, Table 1).

TABLE 1

| | | | SAL-6 sterilization against endospores | | | |
|---|---|---|---|---|---|---|
| Test | Operation Mode | Time (h) | $H_2O_2$ Content (ppm) | *Bacillus stearo-thermophilus* | *Bacillus pumilus* | *Bacillus atrophaeus* |
| #1 | Discontinuous | 2.5 | 600 | — | — | Yes |
| #2 | Discontinuous | 5 | 600 | Yes | — | Yes |
| #3 | Discontinuous | 5 | 1200 | Yes | Yes | Yes |
| #4 | Discontinuous | 2.5 | 1200 | Yes | Yes | Yes |
| #5 | Discontinuous | 2 | 1200 | — | — | Yes |
| #6 | Continuous | 5 | 0 | — | — | — |
| #7 | Continuous | 5 | 1200 | Yes | Yes | Yes |
| #8 | Continuous | 2.5 | 1200 | Yes | Yes | Yes |
| #9 | Continuous | 2 | 1200 | Yes | — | Yes |
| #10 | Combined | 2.5 h discontinuous + 2.5 h continuous | 1200 | Yes | Yes | Yes |
| #11 | Combined | 2 h discontinuous + 1 h continuous | 1200 | Yes | Yes | Yes |
| #12 | Combined | 2 h discontinuous + 0.5 h continuous | 1200 | — | — | Yes |

For a better understanding of the invention, the following examples are provided, without these implying a limitation to the invention.

Example 1. Efficacy of Sterilization Treatment Against Bacterial Endospores

The efficacy of the sterilization treatment was evaluated using spore stretches containing 106 spores of *Bacillus stearothermophilus* (ATCC 7953) (Sigma-Aldrich, Inc.), *Bacillus pumilus* (ATCC 27142) (Sigma-Aldrich, Inc.) and *Bacillus atrophaeus* (cell line 9372) (Crosstex International, Inc.). The spore strips were placed inside sterilization bags, heat-sealed, and be placed in a 100 mL stainless steel sterilization autoclave (Thar Process) equipped with overhead mechanical agitation. $H_2O_2$ was added as an additive to the bottom of the autoclave before its closure, in contents between 600 and 1200 ppm according to Table 1, and without physical contact with the spore strips. The system is heated to 39° C. and pressurized with a $CO_2$ flow of 13.3 bar/min to 140 bar. Depending on the test and according to Table 1, these processing conditions were maintained in discontinuous operation mode (discontinuous in Table 1) and agitation of 700 rpm for a certain period of time between 0 and 5 hours or combined with a subsequent period with continuous flow of $CO_2$ at 5 g/min (continuous in Table 1) through the autoclave for a certain period of time of between 0 and 5 hours. Subsequently, the system was depressurized until it reached atmospheric pressure at a rate of 3.2 bar/min.

The efficacy of the sterilization process and the SAL-6 levels were evaluated qualitatively by visual evaluation of turbidity of the suspensions of the strips in 10 mL in tryptone-soybean broth liquid medium after 7 and 14 days of

Example 2. Sterilization and Foaming of PCL Scaffolds Using Compressed $CO_2$ PCL particles were weighed (1 g) and dosed in a cylindrical mold (length=24.6 mm, inner diameter=17 mm) of Teflon (Brand GmbH). The mold was placed inside a 100 mL stainless steel autoclave (Thar Process). 1200 ppm of hydrogen peroxide are also added at the bottom of the autoclave, without physical contact with the mold. The system is heated to 39° C. and pressurized with a $CO_2$ flow of 13.3 bar/min to 140 bar. These processing conditions were maintained under 700 rpm agitation in combined mode of operation first in discontinuous and then in continuous with $CO_2$ flow at 5 g/min through the autoclave for a period of a) 5 and 0 hours, b) 2.5 and 2.5 hours, and c) 0 and 5 hours, respectively. Subsequently, the system was depressurized to atmospheric pressure at a rate of 3.25 bar/min. In case a), liquid residues of $H_2O_2$ were found at the bottom of the autoclave. In cases b) and c), in which a continuous $CO_2$ flow step was used, the dry porous matrix was obtained, and no liquid remains of $H_2O_2$ were observed in the autoclave.

It is observed (FIG. 1) that in these processing conditions are obtained in all cases porous materials of homogeneous appearance, 65-75% of total porosity, with concave pores and with external morphology modulated by the mold that contains it, and thus the structure of the material obtained in cases a), b) and c) is comparable. Therefore, it is shown that the stage of continuous flow of $CO_2$ used in cases b) and c) does not negatively influence the morphology of the matrix obtained.

The obtaining of SAL-6 sterility levels was confirmed by incorporating strips of *B. pumilus, B. atrophaeus* and *B.*

*stearothermophilus* bioindicators in the autoclave and by monitoring physical variables (pressure, temperature and $CO_2$ flow).

Example 3. Sterilization, Molding and Foaming of PCL Scaffolds with Rhodamine B, Vancomycin Hydrochloride and Pregelled Starch Using Compressed $CO_2$ The experimental conditions of example 2b are repeated for powdery mixtures of i) PCL containing Rhodamine B in proportions 99.5:0.5 by weight, ii) PCL containing vancomycin hydrochloride in proportions 95:5 by weight, iii) PCL containing pregelled starch and vancomycin hydrochloride in proportions 85:10:5 by weight, and iv) vancomycin hydrochloride.

It is observed (FIG. 2) for cases i, ii and iii that at these processing conditions porous materials of homogeneous appearance are obtained, 75-78% of total porosity, with concave pores and with external morphology modulated by the mold that contains it. The load yields of the process are close to 100% according to gravimetric analysis.

Vancomycin release profiles have two distinct stages (FIG. 3). A rapid initial burst-type release during the first hours of release (ca. 4 hours), followed by a lower release that lasts until reaching times greater than 14 days. The presence of pregelled starch acts as a release modulating agent, favoring the release of the drug from the polymer matrix. Vancomycin hydrochloride is not altered with respect to its crystalline form (FIG. 4).

The obtaining of SAL-6 sterility levels was confirmed by incorporating strips of *B. pumilus, B. atrophaeus* and *B. stearothermophilus* bioindicators in the autoclave and by monitoring physical variables (pressure, temperature and $CO_2$ flow).

Example 4. Sterilization and Foaming of Scaffolds of PCL-PLGA of Low Inherent Viscosity Using Compressed $CO_2$ A powdery mixture of PLGA:PCL in weight proportions 50:50 was weighted (1 g) and dosed in cylindrical mold (length=24.6 mm, internal diameter=17 mm) of Teflon (Brand GmbH). The mold is placed inside a 100 mL stainless steel autoclave (Thar Process) provided with agitation (700 rpm). 1200 ppm of hydrogen peroxide are also added at the bottom of the autoclave, without physical contact with the mold. The system is heated to 39° C. and pressurized with a $CO_2$ flux of 13.3 bar/min to 140 bar. These processing conditions were maintained in discontinuous operation mode for a period of time of 2 hours, followed by a continuous flow of $CO_2$ at 5 g/min for 1 hour. The system was then depressurized to 60 bar pressure at a speed of 3.25 bar/min. Subsequently, a flow of liquid $CO_2$ at 4° C. (20 g/min) for 15 minutes reduced the autoclave temperature to 26° C. After keeping the autoclave at 60 bar and 26° C. for 60 minutes, the system was depressurized down to 38 bar at a rate of 20 bar/min and liquid $CO_2$ was added to increase the pressure up to 60 bar again. This cycle of depressurization down to 38 bar and repressurization with liquid $CO_2$ up to 60 bar was carried out another two times. Finally, the system was depressurized until it reached atmospheric pressure at a rate of 20 bar/min.

It is observed (FIG. 5) that in these processing conditions sterile systems are obtained in the form of porous materials of homogeneous appearance, 71% of total porosity, with concave pores and with external morphology modulated by the mold that contains it.

The obtaining levels of sterility SAL-6 was confirmed by incorporating strips of *B. pumilus, B. atrophaeus* and *B. stearothermophilus* bioindicators in the autoclave and by monitoring physical variables (pressure, temperature and $CO_2$ flow). The presence of residual $H_2O_2$ in the treated material was evaluated indirectly by a cytotoxicity test.

Following ISO 10993-5:2009, fibroblasts were used as a model cell line. The material was put in direct contact with the cells for 72 hours at 37° C. in a humidified atmosphere with 5% $CO_2$. The cells exposed to the material presented identical levels of cell viability to those obtained in cells without contact with material (controls) (FIG. 6).

Example 5. Assays with Integrated Foaming, External Molding, and Sterilization of PCL with Compressed $CO_2$ Using Custom Molds Tests carried out under the same experimental conditions as example 3 for powdery mixture of PCL containing Rhodamine B in proportions 99.5:0.5 by weight, in PLA molds processed in different external morphologies customized by additive manufacturing using the Fused Filament Fabrication (FFF) technique. It is observed that after treatment the sterile systems of porous materials obtained are homogeneous in appearance, 70% total porosity, with concave pores and with external morphology modulated by the mold that contains it. The material obtained adapts to the shape of the mold regardless of the angles of inclination on the yz axis (FIG. 7).

Example 6. Sterilization of FFP3 Masks with Supercritical $CO_2$ Suitable for Reuse The efficacy of sterilization treatment was evaluated using a commercial solution of *Bacillus pumilus* spores (ATCC 27142), due to its greater resistance to supercritical sterilization. Mask cutouts (4 cm 2) were inoculated with $10^6$ spores contained in 100 μL of aqueous solution. The samples were placed inside sterilization bags and heat-sealed to be placed in a 600 mL stainless steel autoclave (Novagenesis, Novasterilis Inc.) provided with lower mechanical agitation. $H_2O_2$ was added as an additive at the bottom of the autoclave to avoid direct contact with the masks at a content of 150 ppm. The system is heated to 39° C. and pressurized with a $CO_2$ flow to reach 100 bar. A continuous flow of $CO_2$ of 0 to 10 g/min through the autoclave was maintained for a period of 15 minutes. Subsequently, the system is depressurized to reach atmospheric pressure at a rate of 14.3 bar/min.

The effectiveness of the sterilization method was evaluated by sowing tryptone-soybean agar culture medium and subsequent counting of formed colonies. The results confirmed the effectiveness of the sterilization conditions evaluated, obtaining SAL-6 conditions for the case with a flow of 10 g/min. In cases where continuous $CO_2$ flow was used, the dry material was obtained and no liquid traces of $H_2O_2$ were observed at the bottom of the autoclave.

The morphological properties of the sterilized masks preserved their integrity, allowing their reuse. The material did not undergo significant modifications after undergoing 10 consecutive sterilization processes under the conditions of 10 g/min flow previously described (FIG. 8).

The invention claimed is:

1. A sterilization process, comprising the following steps:

a) introducing the material to be sterilized into an autoclave, and a sterilization additive in concentrations between 100 and 3000 ppm;

b) heating the system to a temperature of 80° C. or less;

c) introducing into the autoclave a compressed gas or supercritical fluid at a pressure of between 40 and 300 bar and at a temperature of between 2° and 80° C., and maintaining these pressure and temperature conditions for between 5 minutes and 24 hours;

d) passing a continuous flow of $CO_2$ of 2 to 500 g/min through the autoclave which is maintained at a pressure of between 40 and 300 bar; and at a temperature of between 20 and 80° C., for between 5 minutes and 24 hours; and e) depressurizing to atmospheric pressure.

2. The sterilization process according to claim 1 for obtaining a sterile, homogeneous porous matrix, of solid or semi-solid consistency, with a porosity greater than 60%, comprising poly(D,L-lactic-co-glycolic) acid, poly(epsilon-caprolactone) or a combination thereof, wherein the material to be sterilized of step a) is a physical mixture of poly(D,L-lactic-co-glycolic) acid, poly(epsilon-caprolactone) or a combination thereof, provided that the depressurization of step e) is carried out in a controlled manner at a rate of between 1 and 50 bar/min down to atmospheric pressure.

3. The sterilization process according to claim 2, wherein the material to be sterilized of step a) is a physical mixture of poly(D,L-lactic-co-glycolic) acid with an inherent viscosity of less than 0.45 dL/g, or is a physical mixture of poly(D,L-lactic-co-glycolic) acid with an inherent viscosity of less than 0.45 dL/g and poly(epsilon-caprolactone), further comprising:

a step d') after step (d) and prior to step (e), comprising passing a continuous flow of liquid $CO_2$ at a temperature of 4° C. or less, from 2 to 500 g/min through the autoclave which is maintained at a pressure of between 40 and 300 bar, for between 5 minutes and 24 hours, and a step e') replacing step (e), comprising controlled depressurization at a rate of between 1 and 19.5 bar/min with cooling by the addition of a compressed liquid, which is gaseous at 25° C. and 1 atmosphere pressure, at a temperature of between −196° and 19° C., down to atmospheric pressure.

4. The sterilization process according to claim 3, further comprising the addition of a biologically active substance in step a).

5. The sterilization process according to claim 3, wherein the supercritical fluid is carbon dioxide.

6. The sterilization process according to claim 3, wherein the sterilization additive is hydrogen peroxide.

7. The sterilization process according to claim 2, wherein in step a) the material is contained in a mold.

8. The sterilization process according to claim 2, further comprising the addition of a biologically active substance in step a).

9. The sterilization process according to claim 2, wherein the supercritical fluid is carbon dioxide.

10. The sterilization process according to claim 2, wherein the sterilization additive is hydrogen peroxide.

11. The sterilization process according to claim 1, further comprising the addition of a biologically active substance in step a).

12. The sterilization process according to claim 1, wherein the supercritical fluid is carbon dioxide.

13. The sterilization process according to claim 1, wherein the sterilization additive is hydrogen peroxide.

14. An implant or scaffold obtainable by a sterilization process comprising the following steps:

a) introducing the implant or scaffold to be sterilized into an autoclave, and a sterilization additive in concentrations between 100 and 3000 ppm;

b) heating the system to a temperature of 80° C. or less;

c) introducing into the autoclave a compressed gas or supercritical fluid at a pressure of between 40 and 300 bar and at a temperature of between 2° and 80° C., and maintaining these pressure and temperature conditions for between 5 minutes and 24 hours;

d) passing a continuous flow of $CO_2$ of 2 to 500 g/min through the autoclave which is maintained at a pressure of between 40 and 300 bar; and at a temperature of between 2° and 80° C., for between 5 minutes and 24 hours; and e) depressurizing to atmospheric pressure.

15. The implant or scaffold according to claim 14, for use as a drug or as a medical device.

16. The implant or scaffold according to claim 15, for use as a drug or as a medical device for bone regeneration.

17. The implant or scaffold according to claim 15, for use as a drug or as a medical device for cartilage regeneration.

18. A method for the release of biologically active substances which comprises utilizing an implant or scaffold obtainable by a sterilization process, wherein the process comprises the following steps:

a) introducing the implant or scaffold to be sterilized into an autoclave, and a sterilization additive in concentrations between 100 and 3000 ppm;

b) heating the system to a temperature of 80° C. or less;

c) introducing into the autoclave a compressed gas or supercritical fluid at a pressure of between 40 and 300 bar and at a temperature of between 2° and 80° C., and maintaining these pressure and temperature conditions for between 5 minutes and 24 hours;

d) passing a continuous flow of $CO_2$ of 2 to 500 g/min through the autoclave which is maintained at a pressure of between 40 and 300 bar; and at a temperature of between 2° and 80° C., for between 5 minutes and 24 hours; and e) depressurizing to atmospheric pressure.

19. A process for bone regeneration or cartilage regeneration comprising utilizing an implant or scaffold obtainable by a sterilization process comprising the following steps:

a) introducing the implant or scaffold to be sterilized into an autoclave, and a sterilization additive in concentrations between 100 and 3000 ppm;

b) heating the system to a temperature of 80° C. or less;

c) introducing into the autoclave a compressed gas or supercritical fluid at a pressure of between 40 and 300 bar and at a temperature of between 2° and 80° C., and maintaining these pressure and temperature conditions for between 5 minutes and 24 hours;

d) passing a continuous flow of $CO_2$ of 2 to 500 g/min through the autoclave which is maintained at a pressure of between 40 and 300 bar; and at a temperature of between 2° and 80° C., for between 5 minutes and 24 hours; and e) depressurizing to atmospheric pressure.

* * * * *